United States Patent [19]
Baker et al.

[11] Patent Number: 5,665,883
[45] Date of Patent: Sep. 9, 1997

[54] ARALKOXY AND ARALKYLTHIO SUBSTITUTED AZACYCLIC COMPOUNDS AS TACHYKININ ANTAGONISTS

[75] Inventors: Raymond Baker, Much Hadham; Angus Murray MacLeod; Eileen Mary Seward, both of Bishops Stortford; Christopher John Swain, Duxford, all of United Kingdom

[73] Assignee: Merck Sharp & Dohme Limited, Hoddesdon, England

[21] Appl. No.: 676,157

[22] PCT Filed: Feb. 6, 1995

[86] PCT No.: PCT/GB95/00228

§ 371 Date: Sep. 26, 1996

§ 102(e) Date: Sep. 26, 1996

[87] PCT Pub. No.: WO95/21819

PCT Pub. Date: Aug. 17, 1995

[30] Foreign Application Priority Data

Feb. 11, 1994 [GB] United Kingdom ............ 9402688

[51] Int. Cl.$^6$ ............ C07D 401/06; A61K 31/445
[52] U.S. Cl. ............ 546/210; 546/216; 546/221
[58] Field of Search ............ 546/210, 216, 546/221; 514/326

[56] References Cited

FOREIGN PATENT DOCUMENTS

| A 0 528 495 | 2/1993 | European Pat. Off. . |
|---|---|---|
| WO A 94 19323 | 9/1994 | WIPO . |

*Primary Examiner*—C. Warren Ivy
*Assistant Examiner*—Charanjit S. Aulakh
*Attorney, Agent, or Firm*—J. Eric Thies; David L. Rose

[57] ABSTRACT

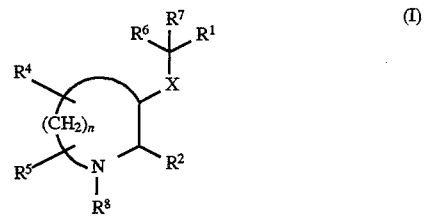

The present invention relates to compounds of formula (I) wherein n is 3 and where any carbon atom of $(CH_2)_n$ may be substituted by $R^4$ and/or $R^5$; X represents O or S; $R^1$ represents $(CH_2)_q$phenyl, wherein q is 0, 1, 2 or 3 which may be optionally substituted in the phenyl ring; $R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted; $R^4$ and $R^5$ each independently represent H, halo, $C_{1-6}$alkyl, oxo, $CO_2R^a$ or $CONR^aR^b$; $R^6$ represents H or $C_{1-6}$alkyl; $R^7$ represents trifluoromethyl, $C_{2-6}$alkenyl, $C_{3-7}$cycloalkyl, $C_{3-7}$cycloalkyl$C_{1-4}$alkyl, $(CH_2)_pNR^9R^{10}$, $CO_2R^{16}$, $CONR^9R^{10}$, $(CH_2)_pCO_2R^{16}$, $(CH_2)_pCONR^9R^{10}$, $(CH_2)_pNR^9COR^{16}$, $(CH_2)_pNHSO_2R^{11}$, $(CH_2)_pOR^{16}$, $(CH_2)_pOC(O)R^9$ or $(CH_2)_pOC_{1-4}$alkylCOR$^{17}$ or $C_{1-6}$alkyl substituted by a hydroxy group; $R^8$ repents H, $COR^a$, $CO_2R^a$, $COCONR^aR^b$, $COCO_2R^a$, $C_{3-7}$cycloalkyl, $C_{3-7}$cycloalkyl$C_{1-4}$alkyl, $C_{1-6}$alkyl optionally substituted by a group selected from $(CO_2R^a$, $CONR^aR^b$, hydroxy, cyano, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{12}$, $CONR^{13}C_{2-6}alkynyl$, $CONR^{13}C_{2-6}alkenyl$, $COCONR^aR^b$, $CONR^aC(NR^b)NR^aR^b$, $CONR^a$heteroaryl, and optionally substituted phenyl or $C_{1-6}$alkyl, optionally substituted by oxo, substituted by an optionally substituted aromatic heterocycle; $R^a$ and $R^b$ each independently represent H, $C_{1-6}$alkyl, trifluoromethyl or phenyl optionally substituted by $C_{1-6}$alkyl, halo or trifluoromethyl. The compounds are of particular use in the treatment of pain, inflammation, migraine and emesis.

10 Claims, No Drawings

ARALKOXY AND ARALKYLTHIO SUBSTITUTED AZACYCLIC COMPOUNDS AS TACHYKININ ANTAGONISTS

This is the U.S. national stage application of PCT/GB95/00228 filed Feb. 26, 1995, and published as WO 9521819 on Aug. 17, 1995.

This invention relates to a class of azacyclic compounds, which are useful as tachykinin antagonists. More particularly, the compounds of the invention comprise an azacyclic ring system substituted by an arylalkoxy or arylalkylthio moiety.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K) (for review see J. E. Maggio, Peptides (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (1987) 8, 506–510], specifically in the transmission of pain in migraine (B. E. B. Sandberg et al, J. Med Chem, (1982) 25, 1009) and in arthritis [Levine et al Science (1984) 226, 547–549]. Tachykinins have also been implicated in gastrointestinal (GI) disorders and diseases of the GI tract such as inflammatory bowel disease [Mantyh et al Neuroscience (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, Eur. J. Pharmacol., (1993) 250, R5–R6]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al, "Neuropeptides in Synovium of Patients with Rheumatoid Arthritis and Osteoarthritis" in J. Rheumatol. (1988)15(12), 1807–10]. Therefore, substance P is believed to be involved in the inflammatory response in diseases such as rheumatoid arthritis and osteoarthritis, and fibrositis [O'Byrne et al, Arthritis and Rheumatism (1990) 33, 1023–8]. Other disease areas where tachykinin antagonists are believed to be useful are allergic conditions [Hamelet et al, Can. J. Pharmacol. Physiol. (1988) 66, 1361–7], immunoregulation [Lotz et al, Science (1988) 241, 1218–21 and Kimball et al, J. Immunol. (1988) 141(10), 3564–9] vasodilation, bronchospasm, reflex or neuronal control of the viscera [Mantyh et al, PNAS (1988) 85, 3235–9] and, possibly by arresting or slowing β-amyloid-mediated neurodegenerative changes [Yankner et al, Science (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, Cancer Research (1992),52, 4554–7].

Substance P may also play a role in demyelinating diseases such as multiple sclerosis and amyotrophic lateral sclerosis [J. Luber-Narod et al, poster C.I.N.P. XVIIIth Congress, 28th Jun.–2nd Jul. 1992], and in disorders of bladder function such as bladder detrusor hyper-reflexia (Lancet, 16th May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists. By virtue of their non-peptide nature, the compounds of the present invention do not suffer from the shortcomings, in terms of metabolic instability, of the known peptide-based tachykinin antagonists discussed above.

The present invention provides a compound of formula (I), or a pharmaceutically acceptable salt or prodrug thereof:

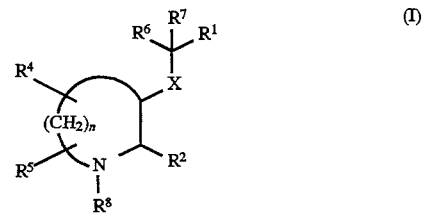

wherein n is 1, 2 or 3 and where any carbon atom of $(CH_2)_n$ may be substituted by $R^4$ and/or $R^5$;

X represents O or S;

$R^1$ represents $(CH_2)_q$phenyl, wherein q is 0, 1, 2 or 3, which may be optionally substituted in the phenyl ring by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, halo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $CO_2R^a$ and $CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, $C_{3-7}$cycloalkyl, $C_{3-7}$cycloalkylC$_{1-4}$alkyl, halo or trifluoromethyl;

$R^4$ and $R^5$ each independently represent H, halo, $C_{1-6}$alkyl, oxo, $CO_2R^a$ or $CONR^aR^b$;

$R^6$ represents H or $C_{1-6}$alkyl;

$R^7$ represents trifluoromethyl, $C_{2-6}$alkenyl, $C_{3-7}$cycloalkyl, $C_{3-7}$cycloalkylC$_{1-4}$alkyl, $(CH_2)_pNR^9R^{10}$, $CO_2R^{16}$, $CONR^9R^{10}$, $(CH_2)_pCO_2R^{16}$, $(CH_2)_pCONR^9R^{10}$, $(CH_2)_pNR^9COR^{16}$, $(CH_2)_pNHSO_2R^{11}$, $(CH_2)_pOR^{16}$, $(CH_2)_pOC(O)R^9$ or $(CH_2)_pOC_{1-4}$alkylCOR$^{17}$ or $C_{1-6}$alkyl substituted by a hydroxy group;

$R^8$ represents H, $COR^a$, $CO_2R^a$, $COCONR^aR^b$, $COCO_2R^a$, $C_{3-7}$cycloalkyl, $C_{3-7}$cycloalkylC$_{1-4}$alkyl, $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, $CONHphenyl(C_{1-4}$alkyl$)$, $COCO_2R^a$, $CONHNR^aR^b$, $C(S)NR^aR^b$, $CONR^aC_{1-6}$alkylR$^{12}$, $CONR^{13}C_{2-6}$alkynyl, $CONR^{13}C_{2-6}$alkenyl, $COCONR^aR^b$, $CONR^aC(NR^b)NR^aR^b$, $CONR^a$heteroaryl, and phenyl optionally substituted by one or more substituents selected from $C_{1-6}$alkyl, $C_{1-6}$alkoxy, halo and trifluoromethyl) or $C_{1-6}$alkyl, optionally substituted by oxo, substituted by an optionally substituted aromatic heterocycle;

$R^a$ and $R^b$ each independently represent H, $C_{1-6}$alkyl, trifluoromethyl or phenyl optionally substituted by $C_{1-6}$alkyl, halo or trifluoromethyl;

$R^9$ and $R^{10}$ each independently represents H or $C_{1-6}$alkyl;

$R^{11}$ represents $NR^{14}R^{15}$ or an optionally substituted aromatic or non-aromatic azacyclic or azabicyclic group;

$R^{12}$ represents $OR^a$, $CONR^aR^b$ or heteroaryl;

$R^{13}$ represents H or $C_{1-6}$alkyl;

$R^{14}$ and $R^{15}$ each independently represent H, $C_{1-6}$alkyl, phenyl optionally substituted by 1, 2 or 3 of $C_{1-6}$alkyl, $C_{1-6}$alkoxy, halo or trifluoromethyl, or phenylC$_{1-4}$alkyl optionally substituted in the phenyl ring by 1, 2 or 3 of $C_{1-6}$alkyl, $C_{1-6}$alkoxy, halo or trifluoromethyl;

$R^{16}$ represents $C_{1-6}$alkyl;

$R^{17}$ represents $C_{1-6}$alkoxy, amino, $C_{1-4}$alkylamino or di($C_{1-4}$alkyl)amino; and p is 1 to 4.

As used herein, the definition of each expression, when it occurs more than once in any structure, is intended to be independent of its definition elsewhere in the same structure.

The alkyl, alkenyl and alkynyl groups referred to with respect to the above formula may represent straight, branched or cyclic groups. Thus, for example, suitable alkyl groups include methyl, ethyl, n- or iso-propyl, n-, sec-, iso- or tert-butyl.

The cycloalkyl groups referred to with respect to the above formula may represent, for example, cyclopropyl, cyclobutyl, cyclopentyl or cyclohexyl. Similarly, cycloalkyl-alkyl groups may be, for example, cyclopropylmethyl.

Suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. In particular, the relative orientation of the 2- and 3- substituents on the azacyclic ring may give rise to cis and trans diastereoisomers, of which the cis stereochemistry is preferred. It is to be understood that all such isomers and mixtures thereof are encompassed within the scope of the present invention.

Preferably n is 2 or 3, more preferably 3.

Preferably X represents O.

Preferably q is 0 and $R^1$ represents substituted phenyl. When $R^1$ is substituted phenyl suitable substituents include nitro, trifluoromethyl, trimethylsilyl, bromo, chloro, fluoro, iodo, cyano, methyl, ethyl, cyclopropyl, vinyl, methoxy, phenoxy, amino and carbonylmethoxy. Preferably $R^1$ represents phenyl substituted by one or more groups selected from methyl, trifluoromethyl, chloro and t-butyl.

Preferably $R^1$ represents disubstituted phenyl, more preferably 3,5-disubstituted phenyl such as 3,5-dichlorophenyl or 3,5-bis(trifluoromethyl)phenyl, or monosubstituted phenyl, such as 3-substituted phenyl, e.g. 3-t-butylphenyl.

Preferably $R^2$ represents unsubstituted benzhydryl, phenyl substituted by halo such as fluoro, for example 4-fluorophenyl, or unsubstituted phenyl, more preferably unsubstituted phenyl.

Preferably $R^4$ and $R^5$ both represent H.

Suitable values for $R^6$ include H, methyl and ethyl. Preferably $R^6$ represents H or methyl, more preferably H.

Preferably $R^7$ represents $C_{1-6}$alkyl substituted by a hydroxy group, such as $CH_2OH$, $CH_2CH_2OH$, $CH(OH)CH_3$ or $C(OH)(CH_3)_2$, more preferably $CH_2OH$.

Other suitable values for $R^7$ include trifluoromethyl or $CO_2R^{16}$ where $R^{16}$ is $C_{1-6}$alkyl, and preferably $CO_2R^{16}$ where $R^{16}$ is methyl.

When $R^8$ represents $C_{1-6}$alkyl, optionally substituted by oxo, substituted by a substituted aromatic heterocycle, suitable substituents in the heterocyclic ring include $C_{1-6}$alkyl, $C_{1-6}$alkoxy, oxo, thioxo, halo, trifluoromethyl, $NR^aR^b$, $NR^aCOR^b$, $CONR^aR^b$, $CO_2R^a$, $SO_2R^a$ and $CH_2OR^a$, where $R^a$ and $R^b$ are as previously defined.

Preferably $R^8$ represents $C_{1-3}$alkyl such as methyl, ethyl or i-propyl substituted by a substituted or unsubstituted aromatic heterocycle. Suitable heterocycles include thienyl, furyl, pyrroyl, pyridyl, pyrazolyl, triazolyl, tetrazolyl, thiazoly, pyrazinyl, pyridazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl.

In one group of compounds according to the invention $R^8$ represents $CH_2$-Het, $CH(CH_3)$-Het, $C(CH_3)_2$-Het or $C(O)$-Het, where Het is pyrrolyl, pyrazolyl, pyrazinyl, pyridazinyl, oxadiazolyl, thiadiazolyl, imidazolyl, benzimidazolyl, benzoxazolyl, benzothiophenyl, benzofuranyl or indolyl.

Preferably $R^8$ represents $CH_2$-Het, $CH(CH_3)$-Het, $C(CH_3)_2$-Het or $C(O)$-Het where Het is substituted or unsubstituted oxazolyl, oxadiazolyl, tetrazolyl, thiazolyl, thiadiazolyl, furanyl, thienyl, triazolyl, pyrazinyl, pyridyl, pyridazinyl, imidazolyl or benzimidazolyl. More preferably Her is triazolyl or triazolyl substituted by oxo.

Other suitable values for $R^8$ include H, $COR^a$, $CO_2R^a$, $COCONR^aR^b$, $COCO_2R^a$, $C_{1-6}$alkyl and $C_{1-6}$alkyl substituted by a group selected from $CO_2R^a$, $CONR^aR^b$, CN, $C(NOH)NR^aR^b$, $CONHphenyl(C_{1-4}$alkyl$)$, optionally substituted phenyl, $CONHNR^aR^b$, $COCONR^aR^b$, $CONR^aC(NH)NH_2$, $CSNR^aR^b$, $CONR^{13}C_{2-6}$alkynyl, $CONR^aC_{1-6}$alkylR$^{12}$ and $CONR^a$heteroaryl.

It will be appreciated that, when $R^8$ comprises a heteroaryl moiety substituted by an oxo or thioxo substituent, different tautomeric forms are possible so that the substituent on the heteroaryl moiety may be represented as =O or —OH, or =S or —SH, respectively. For the avoidance of doubt, all such tautomeric forms are embraced by the present invention.

When $R^{11}$ represents $NR^{14}R^{15}$, $R^{14}$ and $R^{15}$ are preferably, both $C_{1-6}$alkyl such as methyl, ethyl, n-propyl, i-propyl, n-butyl, i-butyl or tert-butyl. More preferably $R^{14}$ and $R^{15}$ will both represent methyl.

When $R^{11}$ represents an aromatic or non-aromatic azacycle or azabicycle it may contain one or more additional heteroatoms selected from O, S and N or groups $NR^{28}$, where $R^{28}$ is H, $C_{1-6}$alkyl or phenyl$C_{1-4}$alkyl, and may be unsubstituted or substituted. Suitable substituents include $C_{1-6}$alkyl, $C_{1-6}$alkoxy, oxo, SH, =S, halo, trifluoromethyl, $NR^aR^b$, $NR^aCOR^b$, $CONR^aR^b$, $CO_2R^a$ and $CH_2OR^a$, where $R^a$ and $R^b$ are as previously defined.

When $R^{11}$ represents an aromatic azacycle or azabicycle, suitable values of $R^{11}$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^{11}$ represents a non-aromatic azacycle or azabicycle, suitable values of $R^{11}$ include morpholinyl, piperdinyl, pyrrolidinyl, piperazinyl, methylpiperazinyl, azanorbornanyl, azabicyclo[2.2.2]octanyl and azabicyclo [3.2.2]nonyl, preferably morpholinyl, pyrrolidinyl, methylpiperazinyl, quinuclidinyl (azabicyclo[2.2.2]octanyl) or azabicyclo[3.2.2]nonyl, more preferably pyrrolidinyl.

A particular sub-class of compounds according to the present invention is represented by compounds of formula (Ia), and pharmaceutically acceptable salts and prodrugs thereof:

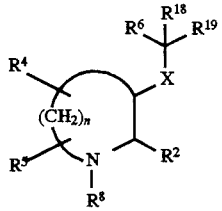

(Ia)

wherein $R^2$, $R^4$, $R^5$, $R^6$, $R^8$, X and n are as defined for formula (I) above;

$R^{18}$ represents trifluoromethyl, $CO_2R^{16}$ or $C_{1-6}$alkyl substituted by a hydroxy group; and $R^{19}$ represents phenyl optionally substituted by 1, 2 or 3 groups selected from $C_{1-6}$alkyl, $C_{2-6}$alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ and —$CONR^aR^b$.

A further sub-class of compounds according to the present invention is represented by compounds of formula (Ib) and pharmaceutically acceptable salts and prodrugs thereof:

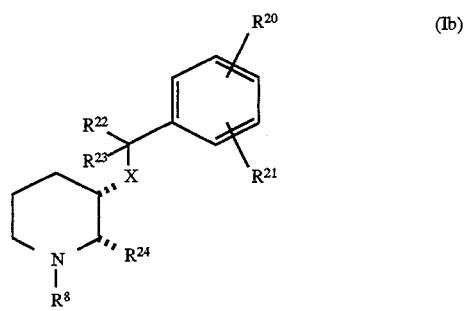

(Ib)

wherein
X represents O or S, preferably O;
$R^8$ is as defined for formula (I);
$R^{20}$ and $R^{21}$ independently represent H $C_{1-6}$alkyl, $C_{2-6}$alkenyl, $C_{2-6}$alkynyl, chloro, bromo, fluoro, iodo, cyano, nitro, trifluoromethyl, trimethylsilyl, $OR^a$, $SR^a$ $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ are as previously defined.
$R^{22}$ is $CH_2OH$, $CF_3$ or $CO_2CH_3$;
$R^{23}$ is H or methyl; and
$R^{24}$ represents phenyl or benzhydryl wherein any of the phenyl rings of the phenyl or benzhydryl moieties may optionally be substituted by halo or trifluoromethyl, preferably unsubstituted phenyl.

Particular values of $R^{20}$ and $R^{21}$ include methyl, ethyl, t-butyl, chloro and trifluoromethyl. Preferably $R^{20}$ and $R^{21}$ are both other than hydrogen and are located at the 3- and 5-positions of the phenyl ring.

A preferred group of compounds according to the present invention are compounds of formula (Ib) wherein $R^8$ is optionally substituted triazolyl.

Specific compounds within the scope of the present invention include:
2-(S)-phenyl-3-(S)-(2,2,2-trifluoro-1-(3-(trifluoromethyl) phenyl)ethoxy) piperidine;
3-(S)-(1-(3,5-bis(trifluoromethyl)phenyl))-1- (carbomethoxy)methyloxy-2-(S)-phenylpiperidine;
3-(S)-(1-(3,5-bis(trifluoromethyl)phenyl)-2- hydroxyethoxy)-2-(S)-phenylpiperidine;
3-(S)-(1-(3,5-bis(trifluoromethyl)phenyl)-2- hydroxyethoxy)-1-(2,3-dihydro-3-oxo-1,2,4-triazol-5-yl) methyl-2-(S)-phenylpiperidine; and pharmaceutically acceptable salts and prodrugs thereof.

For use in medicine, the salts of the compounds of formula (I) will be pharmaceutically acceptable salts. Other salts (such as the dibenzoyltartrate salts) may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising a compound of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as .systemic lupus erythematosus; gastrointestinal (GI) disorders and diseases of the GI tract such as disorders associated with the neuronal control of viscera, ulcerative colitis, Crohn's disease, irritable bowel syndrome and emesis, including acute, delayed or anticipatory emesis such as emesis induced by chemotherapy, radiation, toxins, vital or bacterial infections, pregnancy, vestibular disorders, motion, surgery, migraine, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-$HT_3$ antagonist, such as ondansetron, granisetron or tropisetron, or other anti-emetic medicaments, for example, a dopamine antagonist such as metoclopramide. Additionally, a compound of formula (I) may be administered in combination with an anti-inflammatory corticosteroid, such as dexamethasone. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day; in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 2 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The compounds according to the present invention may be prepared by a process (A) which comprises reacting a compound of formula (II) with a compound of formula (III):

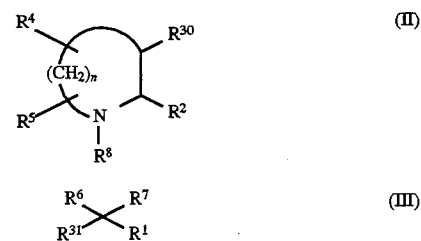

wherein $R^1$, $R^2$, $R^4$, $R^5$, $R^6$, $R^7$, $R^8$ and n are as defined for formula (I), except that, reactive moieties represented by, for example, $R^8$ are replaced by suitable protecting groups, such as t-butoxycarbonyl; and one of $R^{30}$ and $R^{31}$ represents a leaving group and the other of $R^{30}$ and $R^{31}$ represents XH, XH, where X is as defined for formula (I); in the presence of a base, followed by deprotection, if required.

Suitably $R^{30}$ represents XH and $R^{31}$ represents a leaving group.

Suitable leaving groups include halo, e.g. chloro, bromo or iodo, or sulphonate derivatives such as tosylate, mesylate or triflate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, sodium hydride is used.

Alternatively, compounds of formula (I) wherein $R^6$ is H and $R^7$ is $CO_2R^{16}$ may be prepared by a process (B), which comprises reacting a compound of formula (IV) with a compound of formula (V):

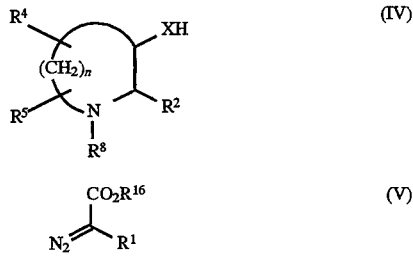

wherein $R^1$, $R^2$, $R^4$, $R^5$, $R^8$, $R^{16}$, X and n are as defined in relation to formula (I) except that when $R^8$ is H it is replaced by a suitable protecting group, such as tert-butoxycarbonyl or benzyl. The reaction is effected in the presence of a catalyst such as rhodium(II)acetate in a suitable solvent, such as a hydrocarbon, for example, toluene at elevated temperature, conveniently at reflux.

Thereafter, the $CO_2R^{16}$ group may be converted to other $R^7$ groups by known methods. Thus, for example, reaction with a Grignard reagent of formula $R^cMgHal$ where $R^c$ is an alkyl group and Hal is as previously defined will give compounds where $R^7$ is a tertiary alcohol. Secondary alcohols may be prepared firstly by reduction of the ester moiety to an aldehyde using, for example, diisobutylaluminium hydride, followed by reaction with either $R^cLi$ or $R^cMgHal$.

The aldehyde may also be used as a precursor for alkenyl intermediates where the group at position $R^7$ has the formula —CH=CHR$^d$, where $R^d$ is $(CH_2)_sNR^9R^{10}$, $(CH_2)_sCO_2R^{16}$, $(CH_2)_sCONR^9R^{10}$ or $(CH_2)_sNR^9COR^{16}$ (where s is 0, 1, or 2 and $R^9$, $R^{10}$ and $R^{16}$ are as previously defined). These compounds may be prepared by a Wittig reaction using, for example, $Ph_3P=CHR^d$ or $(EtO)_3P(O)=CHR^d$. These alkenyl intermediates may be reduced using, for example, catalytic hydrogenation to give compounds wherein $R^7$ is $(CH_2)_pNR^9R^{10}$, $(CH_2)_pCO_2R^{16}$, $(CH_2)_pCONR^9R^{10}$ or $(CH_2)_pNR^9COR^{16}$ and p is 2 to 4.

Compounds wherein $R^7$ is $CONR^9R^{10}$ may be prepared by the reaction of a compound of formula (I) wherein $R^7$ is $CO_2R^{16}$, and $R^{16}$ is methyl, with an amine of the formula $HNR^9R^{10}$ by known methods. Subsequent reduction using, for example, borane in tetrahydrofuran may be used to give a compound wherein $R^7$ is $(CH_2)_pNR^9R^{10}$ in which p is 1. Where one or both of $R^9$ and $R^{10}$ in the resultant amine is a hydrogen atom, the amine may be further converted into a compound wherein $R^7$ is $(CH_2)_pNR^9COR^{16}$ by reaction with, for example, an acyl chloride of the formula $R^{16}COCl$ by known methods.

Compounds wherein $R^7$ is $CH_2OH$ may be prepared by the reduction of a compound of formula (I) wherein $R^7$ is $CO_2R^{16}$, and $R^{16}$ is methyl, using, for example, lithium aluminium hydride. The primary alcohol may be used to prepare a compound of formula (I) wherein $R^7$ is $(CH_2)_pOR^{16}$ and p is 1 by reaction with a halide of the formula $R^{16}Hal$, where Hal is as previously defined in the presence of a suitable base such as sodium hydride.

If a compound of the formula (I) is required in which $R^6$ is an alkyl group it may be prepared via a corresponding compound of the formula-(I) in which $R^7$ is $CO_2R^{16}$ group by reaction with KHMDS and an alkyl iodide, followed, if desired, by conversion of the $CO_2R^{16}$ group as described above.

Alternatively, compounds of formula (I) may be prepared by other interconversion processes which, in particular, vary the group $R^8$. For example, compounds of formula (I) wherein $R^8$ is other than H may be prepared from the corresponding compounds of formula (I) wherein $R^8$ is H by reaction with a reagent suitable to introduce the group $R^8$, for example, a halide or acyl halide, or corresponding mesylate or tosylate, of formula $R^8$-L, where L represents halo, such as chloro, bromo or iodo, methylsulphonate or p-toluenesulphonate, or any other suitable leaving group, in the presence of a base. Suitable bases of use in the reaction include inorganic bases such as alkali metal carbonates, for example, potassium carbonate. Conveniently the reaction is effected in a suitable organic solvent, for example, dimethylformamide.

Compounds of formula (I) wherein $R^8$ is $COR^a$ may be prepared from compounds of formula (I) wherein $R^8$ is H by, for example, reaction with an appropriate acid anhydride.

Compounds of formula (I) wherein $R^8$ is $C_{1-6}$alkyl may be prepared from corresponding compounds of formula (I) wherein $R^8$ is $COR^a$ by reduction using, for example, borane or a borohydride such as sodium cyanoborohydride.

Compounds of formula (I) wherein $R^8$ is $C_{1-6}$alkyl substituted by $CONR^aR^b$ may be prepared from corresponding compounds of formula (I) wherein $R^8$ is $C_{1-6}$alkyl substituted by $CO_2R^a$ by treatment with ammonia or an amine of formula $NR^aR^b$.

Compounds of formula (I) wherein $R^8$ is $C_{1-6}$alkyl substituted by 5-oxadiazolyl may be prepared from compounds of formula (I) wherein $R^8$ is $C_{1-6}$alkyl substituted by $CO2R^a$, where $R^a$ represents $C_{1-6}$alkyl, by reaction with a compound of formula (VI)

wherein $R^{32}$ represents H or a suitable substituent, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

Compounds of formula (I) wherein $R^8$ is $C_{1-6}$alkyl substituted by tetrazolyl may be prepared from compounds of formula (I) wherein $R^8$ is $C_{1-6}$alkyl substituted by cyano by treatment with an alkali metal azide, such as sodium azide.

Compounds of formula (I) wherein $R^8$ is $C_{1-6}$alkyl substituted by thiazolyl may be prepared from compounds of formula (I) wherein $R^8$ is $C_{1-6}$alkyl substituted by $CSNH_2$ by reaction with a compound of formula $Hal-CH_2C(O)-R^{60}$, where Hal is halo, such as bromo,, chloro or iodo, and $R^{60}$ represents H or a suitable substituent.

Compounds of formula (I)wherein $R^8$ is $C_{1-6}$alkyl substituted by thioxotriazolyl may be prepared from compounds of formula (I) wherein $R^8$ is $C_{1-6}$alkyl substituted by $CONHNH_2$ by reaction with a compound of formula $R^{61}NCS$, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU). The reaction is conveniently effected in a suitable orgainc solvent, such as alcohol, e.g. butanol.

Compounds of formula (I) wherein $R^8$ is $C_{1-6}$alkyl substituted by unsubstituted or substituted triazolyl may be prepared from compounds of formula (VII)

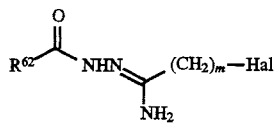
(VII)

wherein Hal is as previously defined, m is 1, 2, 3, 4, 5 or 6 and $R^{62}$ is H or a group suitable as a substituent of the triazole ring, or convertable to such a group under the reaction conditions, in the presence of a base.

Suitable bases of use in the reaction include alkali metal carbonates, such as, for example, potassium carbonate.

Suitably $R^{62}$ represents H, $OCH_3$ (which is converted to an oxo substituent under the reaction conditions) or $CONH_2$.

The reaction is conveniently effected in an anhydrous organic solvent, such as, for example, anhydrous dimethylformamide, preferably at elevated temperature, such as about 60° C.

Compounds of formula (I) wherein $R^8$ represents $C_{1-6}$alkyl substituted by $CONR^aC_{1-6}$alkyl$R^{12}$ or $CONR^a$heteroaryl may be prepared from compounds of formula (I) wherein $R^8$ is $C_{1-6}$alkyl substituted by $CO_2H$ by reaction with an amine of formula $HNR^aC_{1-6}$alkyl$R^{12}$ or $HNR^a$heteroaryl.

The intermediates of formula (II) above wherein $R^{30}$ is SH may be prepared from the corresponding intermediates of formula (II) wherein $R^{30}$ represents OH by treating the latter compound with Lawesson's reagent or phosphorus pentasulphide in a suitable solvent, e.g. pyridine, at ambient or elevated temperatures, suitably at reflux temperature.

Intermediates of formula (II) above wherein $R^{30}$ is OH may be prepared from corresponding compounds of formula (VIII):

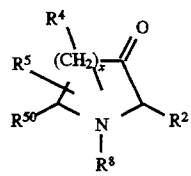
(VIII)

wherein $R^2$, $R^4$, $R^5$ and $R^8$ are as defined for formula (II) above, x is 1 or 2 and $R^{50}$ is an optional carbonyl group, by reduction. Suitable reducing agents will be readily apparent to one skilled in the art and include, for example, metallic hydrides, such as lithium aluminium hydride or, preferably, sodium borohydride.

Intermediates of formula (II) wherein $R^{30}$ is a leaving group may be prepared from compounds of formula (II) wherein $R^{30}$ is OH, for example, by reaction with a thionyl halide, a mesyl halide or a tosyl halide.

Where they are not commercially available, the intermediates of formula (III) above may be prepared by the procedures described in the accompanying Examples or by alternative procedures which will be readily apparent to one skilled in the art.

Compounds of formula (VIII) wherein x is 1, the carbonyl group $R^{50}$ is absent, and $R^5$ represents $CO_2(C_{1-6}$alkyl), may be prepared by reaction of compounds of formula (IX) with compounds of formula (X):

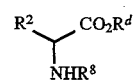
(IX)

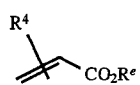
(X)

wherein $R^2$ is as above defined, $R^d$ represents $C_{1-6}$alkyl and $CO_2R^e$ is $R^5$; in the presence of a base.

Suitable bases include alkali metal hydrides, such as sodium hydride, and alkali metal alkoxides, such as sodium butoxide. The reaction is conveniently effected in a suitable organic solvent, such as a hydrocarbon, for example, benzene or toluene, or an ether, for example tetrahydrofuran.

Compounds of formula (VIII) wherein $R^{50}$ is absent and $R^5$ represents $CO_2(C_{1-6}$alkyl) (VIIIB), may be prepared by reaction of a compound of formula (IX) with a compound of formula (XA)

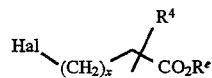
(XA)

wherein x is 1 or 2 and Hal represents halo, such as chloro, bromo or iodo, and $CO_2R^e$ is as above defined, in the presence of a base, as above described.

Further procedures for the preparation of compounds of formula (VIII) using the Dieckmann reaction will be apparent to those skilled in the art and are described in the accompanying examples.

Compounds of formula (VIII) wherein $R^5$ is other than $CO_2(C_{1-6}$alkyl) may be prepared from compounds of formula (VIII) wherein $R^5$ represents $CO_2(C_{1-6}$alkyl) by decarboxylation using, for example, oxalic acid.

Alternatively, compounds of formula (VIII) wherein x is 2 may be prepared from enamines of formula (XI):

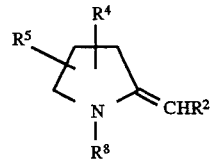
(XI)

according to the method of Cervinka et al, Collect. Czech. Chem. Commun., (1988), 53, 308–10.

Compounds of formula (VIII) wherein x is 2 and the carbonyl group $R^{50}$ is present may be prepared from intermediates of formula (XII):

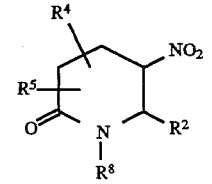
(XII)

by ozonolysis, or by means of the Nef reaction. Suitable reagents and conditions are described in Organic Reactions, 38, 655.

Compounds of formula (VIII) wherein one or both of $R^4$ and $R^5$ represents halo, $C_{1-6}$alkyl, $CONR^aR^b$ or $CO_2R^a$ may be prepared from appropriately substituted analogues of the compounds of formulae (IX), (X) and (XA), or by appropriate interconversion procedures which will be readily apparent to those skilled in the art.

Intermediates of formula (IX) wherein $R^d$ is $C_{1-6}$alkyl (IXA) may be prepared from the corresponding compounds of formula (IX) wherein $R^d$ is H (IXB), by conventional methods.

Intermediates of formula (IXB) may be prepared from the compound of formula (XIII):

by reaction with a compound R²-Hal, wherein R² is as above defined and Hal is halo, such as bromo, chloro or iodo, in the presence of a base, followed by hydrolysis and suitable modification of the nitrogen substituent using conventional methods.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethylammonium chloride.

Hydrolysis is conveniently effected by heating a solution of the product of reaction between the compound of formula (XII) and R²-Hal in concentrated hydrochloric acid, at reflux.

The compound of formula (XIII) is commercially available.

Intermediates of formula (XII) are prepared as described in European Patent Application No. 0 436 334.

Compounds of formula R²-Hal may be prepared according to the procedure described by E. J. Corey, *Tetrahedron Lett.*, (1972), 4339.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, intermediate alcohols of formula (II), wherein $R^{30}$ is OH, may be resolved into their component enantiomers by standard techniques, such as the formation of diastereomeric esters or amides, followed by chromatographic separation or separation by fractional crystallization and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973;, and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the NK1 receptor of less than 150 nM.

The compounds of this invention may be formulated as specifically illustrated at pages 35 to 36 of International Patent Specification No. WO 93/01165.

The following Examples illustrate the preparation of compounds according to the invention.

DESCRIPTION 1

(2S,3S)-1-t-Butyloxycarbonyl-3-hydroxy-2-phenylpiperidine a) 5-Nitro-2-oxo-6-phenylpiperidine A solution of methyl 4-nitrobutyrate (23 g) and benzaldehyde (16 ml) in acetic acid (39 ml) containing ammonium acetate (12.12 g) was heated at reflux under nitrogen for 2 h. The reaction mixture was cooled to 5° C., whereby a pale-yellow solid crystallised. This was isolated by filtration, then dissolved in dichloromethane, washed cautiously with saturated aqueous sodium bicarbonate solution (2×), then dried ($MgSO_4$) and concentrated to leave a yellow solid. Recrystallisation from ethyl acetate provided the product (12.5 g) as a crystalline, white solid. ¹H NMR ($CDCl_3$) δ 7.46–7.26 (m), 6.0 (br s), 5.24 (dd, J=1.4, 7.0 Hz), 4.70 (m), 2.70–2.50 (m), 2.38–2.24 (m).

b) 3-Hydroxy-2-phenylpiperidine

Potassium t-butoxide (1.68 g) was added to a solution of 5-nitro-2-oxo-6-phenylpiperidine (3 g) in a mixture of dichloromethane (50 ml) and methanol (50 ml) and the mixture was cooled to −78° C. under nitrogen. Ozone was bubbled through the solution for 3 h. A yellow-green solution resulted, and TLC indicated no starting material remained. The reaction mixture was purged with oxygen for 5 min to remove excess ozone, then dimethylsulfide (7 ml) was added and the reaction mixture was allowed to warm to 23° C. The solvent was removed in vacuo, and the residue was partitioned between dichloromethane and water. The layers were separated, and the aqueous phase was extracted twice with dichloromethane. The combined organic extracts were washed with brine, then dried ($K_2CO_3$) and concentrated to leave a yellow solid.

This crude material was slurried in dry THF and added to lithium aluminium hydride (1M in THF, 50 ml) then heated at reflux for 12 h. After cooling to 23° C., the reaction mixture was quenched by the cautious addition of water (dropwise) under nitrogen, then 2M sodium hydroxide. The mixture was filtered through a pad of Hyflo, the filtrate was washed with brine, then dried ($K_2CO_3$) and concentrated to leave a yellow solid. Purification by silica-gel chromatography ($CH_2Cl_2$/MeOH/$NH_3$ 97:3:1 then $CH_2Cl_2$/MeOH 95:5) provided the product as a 4:1 mixture of cis- and trans-isomers respectively. ¹H NMR ($CDCl_3$) δ7.44–7.20 (m), 3.84 (2), 3.76 (s), 3.54 (m), 3.4 (s), 3.3 (d, J=8Hz), 3.26 (m), 3.04 (m) 2.78 (ddd, J=2.9, 11.9, 11.9 Hz), 2.70 (ddd, J=2.9, 11.9, 11.9Hz), 2.18–1.78 (m), 1.48 (m). MS (EI) m/z 177 ($M^+$).

c) cis-3-Hydroxy-2-phenylpiperidinium tosylate

The mixture of cis- and trans-isomers of 3-hydroxy-2-phenylpiperidine (Description 1 (b)) and 4-toluenesulfonic acid monohydrate was crystallized from methanol/ethyl acetate to give the product, mp 266°–267° C.

d) cis-3-Hydroxy-2-phenylpiperidine

The tosylate salt (Description 1 (c) above) was dissolved in a mixture of ethyl acetate and 10% aqueous $Na_2CO_3$ with warming. The organic phase was washed with saturated brine, dried ($K_2CO_3$) and evaporated to give the crystalline product, mp 110°–110.5° C.

e) (−)-3-Hydroxy-2-phenylpiperidine cis-3-Hydroxy-2-phenylpiperidine (Description 1 (d)) and (−)dibenzoyltartrate were dissolved in methanol and crystallized by addition of ethyl acetate. The solid was recrystallised from hot methanol to give the hemi dibenzoyltartrate salt, mp 223°–224° C. This was liberated from the salt as described above to give the single enantiomer (+)-cis-3-hydroxy-2-phenylpiperidine, mp 93°–95° C. $[\alpha]^{23}_D$+98.5° (c=1, MeOH). The mother liquors were converted to the free base as described in Description 3 b and crystallization using (+)dibenzoyltartrate in an analogous manner to that described above gave the product, mp 93°–95° C. [a]$^{23}_D$=–97.2° C. (c=1, MeOH).

f) (2S,3S)-1-t-Butyloxycarbonyl-3-hydroxy-2-phenylpiperidine

Di-t-butyldicarbonate (1.36 g, 6.2 mmol) was added to a solution of (–)-3-hydroxy-2-phenylpiperidine (1 g) (Description 1 (e))in dichloromethane (8 ml) under nitrogen and the mixture stirred at 23° C. for 3h. The solvent was removed in vacuo, and the residue purified by silica-gel chromatography using 10–30% ethyl acetate in hexane as eluant to provide the title compound (1.4 g, 89%) as a clear, viscous oil. $^1$H NMR (CDCl$_3$) δ7.50–7.42 (m), 7.40–7.14 (m), 5.36 (d, J=5.6Hz), 4.50 (m), 4.44 (m), 4.12–3.92 (m), 3.02 (ddd, J=3.0, 12.5, 12.5 Hz), 2.87 (ddd, J=3.0, 12.5, 12.5 Hz), 1.88–1.66 (m), 1.46 (s), 1.36 (s).

EXAMPLE 1

2-(S)-Phenyl-3-(S)-(2,2,2-trifluoro-1-(3-(trifluoromethyl)phenyl)ethoxy) piperidine (isomer A)

a) N-[2,2,2-Trifluoro-1-(3-(trifluoromethyl)phenyl)ethylidene]-N'-(2,4,6-triisopropylbenzenesulfonyl)hydrazine 2,2,2-Trifluoro-3'-(trifluoromethyl)acetophenone (3.7 g, 0.15 mol) was dissolved in dichloromethane (15 ml, anhydrous) and the solution was cooled to 0° C. Titanium tetrachloride (15 ml, 1.0M in dichloromethane) was added to the solution dropwise and the resulting ochre suspension was stirred at room temperature for 12 h. 2,4,6-Triisopropylbenzenesulfonyl hydrazine (3.8 g, 0.015 mol) was added to the suspension and the reaction mixture was stirred for 2 h. The mixture was quenched with water and the organic phase was separated, washed with brine, dried and the solvent was removed in vacuo. The resulting solid was purified by column chromatography using 10–25% ethyl acetate in hexane as eluant. This afforded the product as a white crystalline solid (3.9 g). $^1$HNMR (250 MHz, CDCl$_3$) δ 1.10–1.22 (m, 18H, (CH$_3$)$_2$), 2.86 (septet, 1H, CH(CH$_3$)$_2$), 4.02 (septet, 2H, CH(CH$_3$)$_2$), 7.14 (S, 2H, ArH), 7.40–7.48 (m, 2H, ArH), 7.64 (t, 1H, ArH), 7.72–7.80 (m, 1H, ArH), 8.72 (s, 1H, NH).

b) 2,2,2-Trifluoro-3'-(trifluoromethyl)diazoethane

To the compound of a) above (3.6 g, 0.0068 mol) in methanol (15 ml) was added potassium hydroxide (0.77 g, 0.0136 mol) and the mixture was heated at 60° C. for 5 min. A bright orange solution resulted. This solution was cooled and dispersed between ether and water (50 ml). The ethereal phase was washed with sodium bicarbonate (×2), water and brine. The solution was dried (MgSO$_4$) and evaporated to afford an orange oil which was purified by column chromatography on silica using petrol (bp 30° C.) as eluant giving the product (1.5 g) as a volatile orange oil which was used in the next step without further purification.

c) 1-t-Butoxycarbonyl-2-(S)-phenyl-3-(S)-(2,2,2-trifluoro-1-(3-(trifluoromethyl)phenyl)ethoxy) piperidine (isomer A)

To a solution of the product of Description 1 (1.6 g, 5.8 mmol), and rhodium acetate (8 mg), in dry benzene (15 ml), heated at reflux under an atmosphere of dry argon, was added dropwise with stirring over 25 hours, a solution of 2,2,2-trifluoro-3'-(trifluoromethyl)diazoethane (500 mg, 2 mmol) in dry benzene (4 ml), via a syringe pump. The resulting solution Was heated for a further 1 hour, cooled to room temperature, and the solvents evaporated at reduced pressure. The residue was chromatographed on silica (eluent hexane –>5% ethyl acetate in hexane), to afford the the title compound as a colourless oil (10 mg, 1%). $^1$H NMR (250 MHz, CDCl$_3$) Δ 1.32 (9H, s, tBu), 1.44–1.56 (2H, m, CH), 1.64–1.74 (1H, m, CH), 1.75–1.90 (1H, m, CH), 2.60 (1H, dt, J=10, 5 Hz, CH), 3.68–3.88 (2H, m, CHN, +CHO), 4.80 (1H, q, J=7.5 Hz, CH(CF$_3$)), 5.60 (1H, brs, PhCHN), 7.06–7.74 (9H, m, ArH).

d) 2-(S)-Phenyl-3-(S)-(2,2,2-trifluoro-1-(3-(trifluoromethyl)phenyl)ethoxy)piperidine (isomer A)

The compound of c) above (10 mg) was dissolved in methanolic hydrogen chloride and the resulting solution stirred for 12 h. The solvent was evaporated and the residue was recrystallised from ethyl acetate/ether to afford the title compound as a buff-coloured solid (6 mg). $^1$H NMR (250 MHz, DMSO-d$_6$) δ 1.40–1.56 (2H, m, CH), 1.64–1.80 (2H, m, CH), 3.00–3.08 (1H, m, CH), 3.31 (1H, mc, CH), 4.15 (1H, s, CHO), 4.60 (1H, d, J=12 Hz, CHN), 5.38 (1H, q, J=7 Hz, CH(CF$_3$)), 7.40–7.47 (3H, m, ArH), 7.56–7.58 (2H, m, ArH), 7.70 (1H, t, ArH) 7.81 (1H, d, ArH), 8.02 (2H, s, ArH), MS (Cl$^+$) m/z 404 (M$^+$ +1, 40%), 176 (100%).

EXAMPLE 2

2-(S)-Phenyl-3-(S)-(2,2,2-trifluoro-1-(3-(trifluoromethyl)phenyl)ethoxy) piperidine (isomer B)

The second product eluting from the column described in Example 1c was reacted according to the method described in Example 1d and the residue was recrystallised from ethyl acetate/methanol to afford the title compound as white needles: $^1$H NMR (250 MHz, DMSO-d$_6$) δ1.70–1.81 (2H, m, CH), 1.91–2.03 (1H, m, CH), 2.32–2.35 (1H, m, CH), 3.00–3.13 (1H, m, OH), 3.36–3.40 (1H, m, OH), 3.75 (1H, s, CHO), 4.53 (1H, brs, CHN), 5.42 (1H, q, J=7 Hz, CH(CF$_3$)), 7.02 (1H, d, ArH), 7.28–7.32 (7H, m, ArH), 7.64 (1H, d, ArH), 9.0 (1H, brs, NH), 9.8 (1H, brs, NH). MS (Cl$^+$) m/z 404 (M$^+$ +1, 40%), 176 (100%).

EXAMPLE 3

3-(S)-(1-(3,5-Bis(trifluoromethyl)phenyl)-1-(carbomethoxy) methyloxy)-2-(S)-phenylpiperidine (isomer A)

(a) Methyl 3,5-bis(trifluoromethyl)phenylacetate 3,5-Bis(trifluoromethyl)phenylacetic acid (10.0 g, 36.7 mmol), was dissolved in methanol (150 ml). The solution was cooled to 4° C. under an atmosphere of dry nitrogen, and thionyl chloride (10 ml) was added dropwise with vigorous stirring over 30 minutes. The mixture was warmed to room temperature, and then stirred for 1 hour. The solvents were evaporated at reduced pressure, the residue dissolved in ether (150 ml), washed with saturated aqueous NaHCO$_3$, dried (Na$_2$SO$_4$), and evaporated to afford the title compound (10.5 g, 100%), as a colourless oil, used without further purification.

(b) Methyl 2-(3,5-bis(trifluoromethyl)phenyl)-2-diazoacetate

To methyl 3,5-bis(trifluoromethyl)phenylacetate (43.5 g, 160 mmol), in dry acetonitrile (250 ml), cooled to –5° C., was added 2,4,6-triisopropylbenzenesulfonyl azide (52.7 g). To the resulting solution was added 1,8-diazabicyclo[5.4.0]undec-7-ene (25.5 ml), and the mixture was stirred at −5° C. for 1 hour. The mixture was warmed to room temperature, and then stirred for 0.5 hour. The solvents were evaporated at reduced pressure and the residue chromatographed on silica (eluent 5% ether/60–80 bp petrol), to afford the the title compound (45.6 g, 91%) as yellow prisms. I.R. (film, NaCl) n 1740, 2140 cm$^{-1}$.

(c) 3-(S)-(1-(3,5-Bis(trifluoromethyl)phenyl)-1-(carbomethoxy)methyloxy)-1-t-butoxycarbonyl-2-(S)-phenylpiperidine (isomers A and B)

To a solution of the product of Description 1 (2 g, 7 mmol), and rhodium acetate (8 mg), in dry benzene (10 ml), heated at reflux under an atmosphere of dry argon, was added dropwise with stirring over 25 hours, a solution of methyl 2-(3,5-bis(trifluoromethyl)phenyl)-2-diazoacetate (1.5 g, 5 mmol) in dry benzene (4 ml), via a syringe pump. The resulting solution was heated for a further 1 hour, cooled to room temperature, and the solvents evaporated at reduced pressure. The residue was chromatographed on silica (eluent 5% ethyl acetate in petrol), to afford the the title compound (as a mixture of inseparable isomers) as a colourless oil (2 g, 50%). $^1$HNMR (250 MHz, CDCl$_3$) δ 1.12 (9H, s, tBu$_{isomer\ A}$), 1.16 (9H, s, tBu$_{isomer\ A}$), 1.2–1.8 (8H, m), 2.40–2.60 (2H, m) 3.42 (3H, s, COOCH$_3$ $_{isomer\ A}$), 3.50 (3H, s, COOCH$_3$ $_{isomer\ B}$), 3.58–3.70 (4H, m), 4.80 (1H, s, C$\underline{H}$COOCH$_{3\ isomer\ B}$), 4.94 (1H, s, C$\underline{H}$COOCH$_3$ $_{isomer\ A}$), 5.23 (1H, d, J=7Hz, PhC$\underline{H}$N$_{isomer\ B}$), 5.42 (1H, d, J=7Hz, PhCH-N$_{isomer\ A}$), 6.90–7.32 (10H, m, ArH), 7.46 (2H, s, ArH)), 7.50 (1H, s, ArH), 7.56 (1H, 1H, ArH), 7.62 (2H, s, ArH).

(d) 3-(S)-(1-(3,5-Bis(trifluoromethyl)phenyl)-1-(carbomethoxy)methyloxy)-2-(S)-phenylpiperidine The mixture of isomers referred to in (c) above was dissolved in methanolic hydrogen chloride and the resulting solution was stirred at room temperature for 4 h. The solvent was removed in vacuo and the residue was dispersed between ethyl acetate and aqueous sodium bicarbonate. The organic layer was washed with water, brine, then dried (MgSO$_4$) and evaporated at reduced pressure. The residual oil was purified by medium pressure chromatography using 5% methanol in dichloromethane as eluent. This afforded isomer A (62 mg) as a clear oil. This was dissolved in methanolic hydrogen chloride and the solvent was removed in vacuo. The resulting solid was recrystallised from ethyl acetate/ether to afford the title compound as colorless crystals: $^1$H NMR (250 MHz, DMSO-d$_6$) δ 1.62–1.79 (3H, m), 1.98–2.05 (1H, m), 3.00–3.16 (1H, m), 3.26 (3H, s, COOCH$_3$), 3.32 (1H, mc), 4.15 (1H, brs, CHO), 4.59 (1H, brs, CHN), 5.44 (1H, s, C$\underline{H}$COOCH$_3$), 7.40–7.47 (3H, m, ArH), 7.54–7.56 (2H, m, ArH), 8.12 (1 H, s, ArH), 8.17 (2H, s, ArH), 9.04 (1 H, brs, NH), 9.84 (1 H, brs, NH). MS (CI$^+$) m/z 462 (M$^+$ +1, 100%), 176 (75)

EXAMPLE 4

3-(S)-(1-(3,5-Bis(trifluoromethyl)phenyl)-1-(carbomethoxy)methyloxy)-2-(S)-phenylpiperidine (isomer B)

The second product eluting from the column described in Example 3d was converted to the hydrochloride salt and was recrystallised from ethyl acetate/ether to afford the title compound as a white solid: $^1$H NMR (250 MHz, DMSO-d$_6$) δ 1.72–1.86 (2H, m), 2.12–2.23 (2H, m), 3.00–3.17 (1H, m), 3.32–3.40 (1H, m), 3.65 (3H, s, COOCH$_3$), 3.99 (1H, brs, CHO), 4.53 (1H, brs, CHN), 5.17 (1H, s, C$\underline{H}$COOCH$_3$), 7.17–7.24 (3H, m, ArH), 7.29–7.32 (2H, m, ArH), 7.68 (2H, s, ArH), 8.00 (1H, s, ArH), 9.04 (1H, brs, NH), 9.84 (1H, brs, NH). MS (CI$^+$) m/z462 (M$^+$ +1, 100%), 176 (75)

EXAMPLE 5

3-(S)-(1-(3,5-Bis(trifluoromethyl)phenyl)-2-hydroxyethoxy)-2-(S)-phenylpiperidine (isomer A)

a) 3-(S)-(1-(3,5-Bis(trifluoromethyl)phenyl)-2-hydroxyethoxy)-1-butoxycarbonyl-2-(S)-phenylpiperidine (isomer A)

To the compound of Example 3c (mixture of inseparable isomers A and B) (1.3 g), dissolved in diethyl ether (30 ml) was added lithium borohydride (46 mg) portionwise. The resulting suspension was stirred for 30 min, quenched with water and the organic phase was separated, washed with brine, dried and the solvent was removed in vacuo. The resulting clear oil was purified by column chromatography using 10–20% ethyl acetate in hexane as eluant. This afforded the product (isomer A) as a clear oil (0.51 g). $^1$H NMR (360 MHz, CDCl$_3$)δ 1.42 (9H, s, (CH$_3$)$_3$), 1.47–1.60 (3H, m, OH+2×CH), 1.73–1.78 (1H, m, CH), 1.93–2.04 (1 H, m, OH), 2.79 (1 H, dt, J=12, 3.5 Hz, C$\underline{H}$N), 3.50–3.57 (2H, m, CH$_2$OH), 3.71–3.77 (1 H, brs, CHO), 3.89–3.92 (1H, brs, CHN), 4.69 (1H, t, J=6.0 Hz, C$\underline{H}$CH$_2$OH), 5.60 (1H, brs, PhCHN), 7.28–7.40 (3H, m, ArH), 7.57–7.59 (2H, m, ArH), 7.81 (2H, s, ArH), 7.83 (1H, s, ArH). MS (CI$^+$) m/z 534 (M$^+$ +1, 40%), 178 (100)

b) 3-(S)-(1-(3,5-Bis(trifluoromethyl)phenyl)-2-hydroxyethoxy)-2-(S)-phenylpiperidine (isomer A)

The compound of a) above was dissolved in methanolic hydrogen chloride and the resulting solution was stirred for 12 h at room temperature. The solvent was removed in vacuo and the resulting solid was recrystailised from ethyl acetate to afford the title compound as a white crystalline solid. $^1$H NMR (250 MHz, DMSO-d$_6$) δ 1.54–1.82 (4H, m), 3.00–3.11 (3H, m, C$\underline{H}$$_2$OH +C$\underline{H}$N), 3.32 (1H, mc), 4.00 (1H, brs, CHO), 4.27 (1H, brt, OH), 4.94 (1H, brs, CHN), 4.61 (1H, brt, C$\underline{H}$CH$_2$OH ), 7.42–7.49 (3H, m, ArH), 7.57–7.59 (2H, m, ArH), 8.01 (1 H, s, ArH), 8.03 (2H, s, ArH), 9.04 (1H, brs, NH), 9.84 (1H, brs, NH). MS (CI$^+$) m/z434 (M$^+$ +1, 100%), 176 (50)

EXAMPLE 6

3-(S)-(1-(3,5-Bis(trifluoromethyl)phenyl)-2-hydroxyethoxy)-2-(S)-phenylpiperidine (isomer B)

The second product eluting from the column described in Example 5a was reacted according to the method described in Example 5b to afford the title compound as a white solid: $^1$H NMR (360 MHz, DMSO-d$_6$) δ 1.65–1.69 (2H, m), 2.16–2.20 (1H, m), 2.32–2.36 (1H, m), 3.08 (1H, mc), 3.32 (1H, mc), 3.34–3.41 (2H, m, C$\underline{H}$$_2$OH ), 3.56 (1 H, brs, CHO), 4.47 (1H, brs, CHN), 4.77–4.80 (1H, m, C$\underline{H}$CH$_2$OH ), 5.42 (1H, brs, CH$_2$OH) 7.38–7.40 (3H, m, ArH), 7.40 (2H, s, ArH), 7.50–7.52 (2H, m, ArH), 7.85 (1H, s, ArH), 9.50 (1H, brs, 2×NH). MS (CI$^+$) m/z 434 (M$^+$ +1, 90%), 178 (100)

EXAMPLE 7

3-(S)-(1-(3,5-Bis(trifluoromethyl)phenyl)-2-hydroxyethoxy)-1-(2,3-dihydro-3-oxo-1,2,4-triazol-5-yl)methyl-2-(S)-phenylpiperidine.

a) N-Carbomethoxy-2-chloroacetamidrazone

Sodium methoxide (20 ml, 1M) was added to a solution of chloroacetonitrile (54.1 g) in anhydrous methanol (100 ml) at 0° C. The mixture was stirred at room temperature for 30 min and then neutralised with acetic acid (1.2 ml). Methyl hydrazinocarboxylate (64.5 g, predistilled in vacuo) was dissolved in warm dimethylformamide (35 ml) and methanol (300 ml) and was added to the reaction mixture at 0° C. The mixture was stirred for 30 min. and the crystalline solid which had formed was removed by filtration and washed with ethyl acetate to give the title compound: mp 138°–140° C.

b) 3-(S)-(1-(3,5-Bis(trifluoromethyl)phenyl)-2-hydroxyethoxy)-1-(2,3-dihydro-3-oxo-1,2,4-triazol-5-yl)methyl-2-(S)-phenylpiperidine The compound of Example 6 (190 mg), potassium carbonate (232 mg), and N-carbomethoxy-2-chloroacetamidrazone (67 mg) were suspended in dimethylformamide (1.3 ml) and the reaction mixture was heated at 60° C. for 2 h. The mixture was then diluted with xylene (10 ml) and the mixture was heated at 140° C. for 2 h. The solvents were removed in vacuo and the residue was suspended in ethyl acetate; the inorganics were removed by filtration through celite and the filtrate was concentrated in vacuo. The residue was purified by medium pressure chromatography (Lobar) using 2–6% methanol in dichloromethane as eluent. The product was recrystallised from ethyl acetate to afford a white solid. MS (Cl+) m/z 531 (M+ +1, 30%), 160 (100).

We claim:

1. A compound of formula (I), or a pharmaceutically acceptable salt thereof:

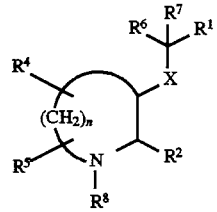

(I)

wherein n is 3 and where any carbon atom of $(CH_2)_n$ may be substituted by $R^4$ and/or $R^5$;

X represents O or S;

$R^1$ represents $(CH_2)_q$phenyl, wherein q is 0, 1, 2 or 3, which may be optionally substituted in the phenyl ring by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, halo, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $CO_2R^a$ and $CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, $C_{3-7}$cycloalkyl, $C_{3-7}$cycloalkyl$C_{1-4}$alkyl, halo or trifluoromethyl;

$R^4$ and $R^5$ each independently represent H, halo, $C_{1-6}$alkyl, oxo, $CO_2R^a$ or $CONR^aR^b$;

$R^6$ represents H or $C_{1-6}$alkyl;

$R^7$ represents trifluoromethyl, $C_{2-6}$alkenyl, $C_{3-7}$cycloalkyl, $C_{3-7}$cycloalkyl$C_{1-4}$alkyl, $(CH_2)_p$ $NR^9R^{10}$, $CO_2R^{16}$, $CONR^9R^{10}$, $(CH_2)_pCO_2R^{16}$, $(CH_2)_p$ $CONR^9R^{10}$, $(CH_2)_pNR^9COR^{16}$, $(CH_2)_pNHSO_2R^{11}$; $(CH_2)_pOR^{16}$, $(CH_2)_pOC(O)R^9$ or $(CH_2)_pOC_{1-4}$alkyl$COR^{17}$ or $C_{1-6}$alkyl substituted by a hydroxy group;

$R^8$ represents H, $COR^a$, $CO_2R^a$, $COCONR^aR^b$, $COCO_2R^a$, $C_{3-7}$cycloalkyl, $C_{3-7}$cycloalkyl$C_{1-4}$alkyl, $C_{1-6}$alkyl optionally substituted by a group selected from ($CO_2R^a$, $CONR^aR^b$, hydroxy, cyano, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}$alkyl$R^{12}$, $CONR^{13}C_{2-6}$alkynyl, $CONR^{13}C_{2-6}$alkenyl, $COCONR^aR^b$, $CONR^aC(NR^b)NR^aR^b$, $CONR^a$heteroaryl, and phenyl optionally substituted by one or more substituents selected from $C_{1-6}$alkyl, $C_{1-6}$alkoxy, halo and trifluoromethyl) or $C_{1-6}$alkyl, optionally substituted by oxo, substituted by an optionally substituted aromatic heterocycle;

$R^a$ and $R^b$ each independently represent H, $C_{1-6}$alkyl, trifluoromethyl or phenyl optionally substituted by $C_{1-6}$alkyl, halo or trifluoromethyl;

$R^9$ and $R^{10}$ each independently represents H or $C_{1-6}$alkyl;

$R^{11}$ represents $NR^{14}R^{15}$ or an optionally substituted aromatic or non-aromatic azacyclic or azabicyclic group;

$R^{12}$ represents $OR^a$, $CONR^aR^b$ or heteroaryl;

$R^{13}$ represents H or $C_{1-6}$alkyl;

$R^{14}$ and $R^{15}$ each independently represent H, $C_{1-6}$alkyl, phenyl optionally substituted by 1, 2 or 3 of $C_{1-6}$alkyl, $C_{1-6}$alkoxy, halo or trifluoromethyl, or phenyl$C_{1-4}$alkyl optionally substituted in the phenyl ring by 1, 2 or 3 of $C_{1-6}$alkyl, $C_{1-6}$alkoxy, halo or trifluoromethyl;

$R^{16}$ represents $C_{1-6}$alkyl;

$R^{17}$ represents $C_{1-6}$alkoxy, amino, $C_{1-4}$alkylamino or di($C_{1-4}$alkyl)amino; and p is 1 to 4.

2. A compound as claimed in claim 1 of formula (Ia), or a pharmaceutically acceptable salt thereof:

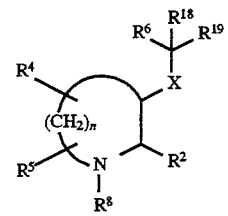

(Ia)

wherein $R^2$, $R^4$, $R^5$, $R^6$, $R^8$, X and n are as defined in claim 1;

$R^{18}$ represents trifluoromethyl, $CO_2R^{16}$ or $C_{1-6}$alkyl substituted by a hydroxy group; and $R^{19}$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, —$SR^a$, —$SOR^a$, —$SO_2R^a$, —$NR^aR^b$, —$NR^aCOR^b$, —$NR^aCO_2R^b$, —$COR^a$, —$CO_2R^a$ and —$CONR^aR^b$.

3. A compound as claimed in claim 1 formula (Ib) or a pharmaceutically acceptable salt thereof:

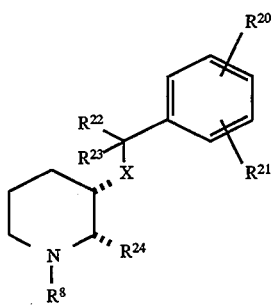

(Ib)

wherein

X and $R^8$ are as defined in claim 1;

$R^{20}$ and $R^{21}$ independently represent H $C_{1-6}$alkyl, $C_{2-6}$alkenyl, $C_{2-6}$alkynyl, chloro, bromo, fluoro, iodo, cyano, nitro, trifluoromethyl, trimethylsilyl, $OR^a$, $SR^a$ $SOR^a$, $SO_2R^a$, $NR^aR^b$, $NR^aCOR^b$, $NR^aCO_2R^b$, $COR^a$, $CO_2R^a$ or $CONR^aR^b$;

$R^{22}$ is $CH_2OH$, $CF_3$ or $CO_2CH_3$;

$R^{23}$ is H or methyl; and $R^{24}$ represents phenyl or benzhydryl wherein any of the phenyl rings of the phenyl or benzhydryl moieties may optionally be substituted by halo or trifluoromethyl.

4. A compound selected from:

2-(S)-phenyl-3-(S)-(2,2,2-trifluoro-1-(3-(trifluoromethyl) phenyl)ethoxy) piperidine;

3-(S)-(1-(3,5-bis(trifluoromethyl)phenyl))-1-(carbomethoxy)methyloxy-2-(S)-phenylpiperidine;

3-(S)-(1-(3,5-bis(trifluoromethyl)phenyl)-2-hydroxyethoxy)-2-(S)-phenylpiperidine;

3-(S)-(1-(3,5-bis(trifluoromethyl)phenyl)-2-hydroxyethoxy)-1-(2,3-dihydro-3-oxo-1,2,4-triazol-5-yl)methyl-2-(S)-phenylpiperidine;

or a pharmaceutically acceptable salt thereof.

5. A pharmaceutical composition comprising a compound as claimed in claim 1 in association with a pharmaceutically acceptable carrier or excipient.

6. A method for the treatment or prevention of physiological disorders associated with an excess of tachykinins, which method comprises administration to a patient in need thereof of a tachykinin reducing amount of a compound according to claim 1, or a pharmaceutically acceptable salt or prodrug thereof.

7. A method according to claim 6 for the treatment or prevention of pain or inflammation.

8. A method according to claim 6 for the treatment or prevention of migraine.

9. A method according to claim 6 for the treatment or prevention of emesis.

10. A process for the preparation of a compound of formula (I) which comprises:

(A) reacting a compound of formula (II) with a compound of formula (III):

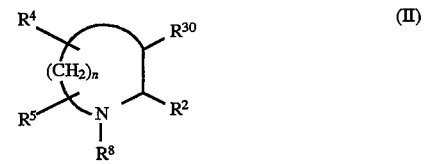

wherein $R^1$, $R^2$, $R^4$, $R^5$, $R^6$, $R^7$, $R^8$ and n are as defined in claim 1, or a protected derivative thereof, and one of $R^{30}$ and $R^{31}$ represents a leaving group and the other of $R^{30}$ and $R^{31}$ represents XH, where X is as defined in claim 1; in the presence of a base; or (B) wherein $R^6$ is H and $R^7$ is $CO_2R^{16}$, by reacting a compound of formula (IV) with a compound of formula (V):

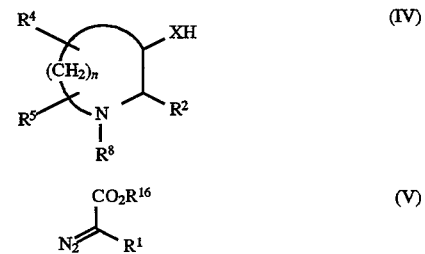

wherein $R^1$, $R^2$, $R^4$, $R^5$, $R^8$, $R^{16}$, X and n are as defined in claim 1, or a protected derivative thereof; or (C) by interconversion of a compound of formula (I) into another compound of formula (I);

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resultant compound of formula (I) or a salt thereof into a pharmaceutically acceptable salt thereof.

* * * * *